(12) United States Patent
Lafayette et al.

(10) Patent No.: US 10,550,436 B2
(45) Date of Patent: Feb. 4, 2020

(54) USING A BREED MATCHING DATABASE AND GENETIC MARKERS FOR COLOR, CURIOSITY, SPEED AND GAIT TO BREED OFFSPRING WITH PREDETERMINED TRAITS

(71) Applicants: Christa Lafayette, Menlo Park, CA (US); Henry Wilfred Lopez, Napa, CA (US); Adam Freund, Menlo Park, CA (US)

(72) Inventors: Christa Lafayette, Menlo Park, CA (US); Henry Wilfred Lopez, Napa, CA (US); Adam Freund, Menlo Park, CA (US)

(*) Notice: Subject to any disclaimer, the term of this patent is extended or adjusted under 35 U.S.C. 154(b) by 467 days.

(21) Appl. No.: 14/818,302

(22) Filed: Aug. 4, 2015

(65) Prior Publication Data

US 2017/0037482 A1    Feb. 9, 2017

Related U.S. Application Data

(60) Provisional application No. 62/033,093, filed on Aug. 4, 2014.

(51) Int. Cl.
*C12Q 1/6888* (2018.01)
*G16B 20/00* (2019.01)
*A01K 29/00* (2006.01)

(52) U.S. Cl.
CPC ............ *C12Q 1/6888* (2013.01); *A01K 29/00* (2013.01); *G16B 20/00* (2019.02); *C12Q 2600/124* (2013.01)

(58) Field of Classification Search
None
See application file for complete search history.

(56) References Cited

U.S. PATENT DOCUMENTS

2012/0059235 A1*  3/2012  Davies ................ A01K 11/008
                                                                600/364

OTHER PUBLICATIONS

Goddard, M. E. et al.; "Mapping genes for complex traits in domestic animals and their use in breeding programmes"; Nature Reviews Genetics; vol. 10, Jun. 2009; p. 381-391.*
Haberland, A. M.; "Integration of genomic information into sport horse breeding programs for optimization of accuracy of selection"; Animal (2012), 6:9, pp. 1369-1376.*
Hill, E. W.; "A Sequence Polymorphism in MSTN Predicts Sprinting Ability and Racing Stamina in Thoroughbred Horses"; PLoS One 5(1): e8645; vol. 5, Issue 1, Jan. 2010; p. 1-6.*
Hill, E. W. et al; Horses for Courses: a DNA-based Test for Race Distance Aptitude in Thoroughbred Racehorses; Recent Patents on DNA & Gene Sequences, 2012, 6, 203-208.*
Schröder, Wiebke, Andreas Klostermann, and Ottmar Distl. "Candidate genes for physical performance in the horse." The Veterinary Journal 190.1 (2011): 39-48.*

* cited by examiner

*Primary Examiner* — G Steven Vanni
(74) *Attorney, Agent, or Firm* — Clark & Elbing LLP

(57) ABSTRACT

The methods of the present invention are based upon the gathering of information from various sources about animals. The information is based upon laboratory testing, genetic analysis and observations by owners and/or trainers about various traits that can be readily observed. Based upon this collection of information, one method generates Performance Index which scores or ranks an animal in terms of how well an animal might function for the intended purpose. Other methods include the ability to selection an optimum breeding pair from one or more stallions and/or one or more mares that would likely produce an offspring with the desired traits.

9 Claims, 3 Drawing Sheets

Fig. 1

ETALON
DIAGNOSTICS

HOME    ABOUT    SERVICES    CONTACT    PARTICIPATE    BLOG

Etalon Owner Survey

Stay Informed - Sign up for our
Quarterly Newsletter.

First Name
Last Name
E-mail
Subscribe

Please answer the following questions about your horse to the best of your ability:

1) On a scale of 1 to 10 would you rate your horse [NAME] a "show jumper"?

(1 = not a jumper, 5 = average jumper, 10 = incredible jumper)

1   3   5   7   10

2) Is this horse a competing FEI champion?
   ○ yes    ○ no

2a) If yes, at what level?   [enter level]

3) Please submit additional scores and comments here:

[Upload scores]

ETALON DIAGNOSTICS

ETALON DIAGNOSTICS

Fig. 2

Fig. 3
| Normal Horse | Affected Horse Example 1 | Affected Horse Example 2 |
|---|---|---|
| 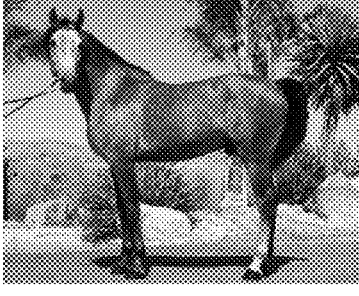 | 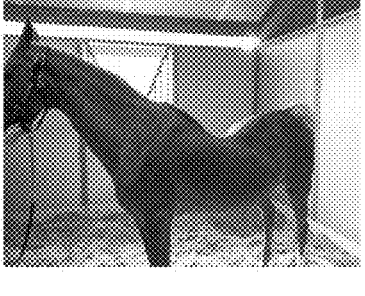 | 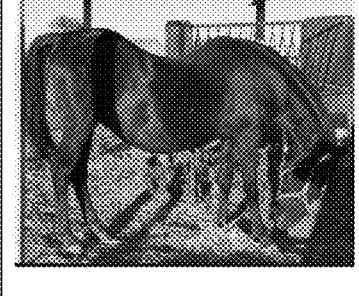 |
| Genotype: TC/GA/CC/GA | Genotype: TT/GG/TT/GG | Genotype: TT/GG/TT/GG |

USING A BREED MATCHING DATABASE AND GENETIC MARKERS FOR COLOR, CURIOSITY, SPEED AND GAIT TO BREED OFFSPRING WITH PREDETERMINED TRAITS

This application claims the benefit of U.S. Provisional Application No. 62/033,093 filed on Aug. 4, 2014. The entire disclosure of the above application is incorporated herein by reference.

A. BACKGROUND

For hundreds or even thousands of years, when an animal such as a horse, cow, sheep, dog, camel, etc. was to be sold, the purchaser had to rely, to a large extent, on the honesty of the seller to communicate accurately the health, age, abilities and pedigree of the animal.

Additionally, the purchaser could rely on his own experience and those physical traits that could be easily observed. For instance, age can be estimated by an inspection of the teeth by an experienced veterinarian, prior to the purchase of a horse. In addition, hooves and joint condition can be checked visually, the coat can be checked for overall condition and any parasites, and other traits can be evaluated physically, visually and behaviorally.

As technology and veterinary science has advanced, clinical laboratory testing can be used to help determine the parentage, health and any pertinent ongoing infections in the animal. Just as in humans, blood work can be done to assess the health of the animal such as measuring blood sugar levels, blood urea nitrogen, amylase, total calcium, and many other clinical lab values. Equipment manufacturers have also developed new equipment which can be configured to allow X-rays, CAT scans, PET scans and most other advanced imaging techniques with horses and other large animals. Various veterinary schools have advanced the understanding of clinical medicine pertaining to animals. For example, Auburn University College of Veterinary Medicine has instituted the Equine Health Research Program to improve equine health through high quality research.

However, these techniques are based on morphological characteristics that can be evaluated by observing and measuring existing structures of various tissues in the body as they currently appear. Based upon these observations and measurements, an evaluation of the physical condition and age of an animal can be made. However, these measurements don't provide any indication of the potential physical skills of the animals nor of the predisposition to future good health or demise. Furthermore, future health and physical problems can only be anticipated based upon existing clinical indicators and not predispositions to disease be they mental or physical.

B. NEED FOR A MORE COMPREHENSIVE METHOD OF EVALUATION

There are a number of animals that are raised and trained to be show and/or race animals (performance and service). In particular, horses and dogs fall into this category. Horses are trained in dressage, jumping, racing, reining, pulling carts and carriages, trial, cutting, ranch, vaulting, endurance and so on. Dogs are trained and evaluated for field events, police work, military work, search and rescue, farm work, and even as guide dogs for the deaf, blind, and mentally disabled. For example, greyhounds are utilized in track racing.

The American Kennel Club (AKC) and the United States Equestrian Federation (USEF) both conduct shows, trials and field events for dogs and horses respectively, in which various skills, traits and behavioral characteristics are evaluated such as tracking, agility conformation and field events. Dogs that have a well-recognized and award winning pedigree, physical appearance and have demonstrated winning physical and behavioral traits can be worth many thousands of dollars for the dog or horse itself as well as competition and stud or breeding fees.

However, it is only after the animals are older and been through intensive training and have been evaluated by participating in any number of shows, trials and events can the true value of such an animal be determined.

Even if an animal comes from a championship blood line there is no guarantee that the animal itself will be a champion, suitable/capable for the chosen discipline or appropriate for breeding. There is a critical need for a method to evaluate animals as possible champions, or having the appropriate service or athletic capabilities much earlier in life from a purchasing concern, breeding concern, and as a means to determine a cost effective approach to raising and training working service dogs or competition horses.

C. BRIEF SUMMARY OF THE INVENTION

The present invention is several methods which are based upon the gathering of information from various sources and using that information to: a. assess the existing skills of the animal, b. the likelihood of that animal developing a serious or deadly disease or pathology, c. assessing the likelihood that the animal will respond to training directed towards developing a desired skill and d. another method of the present invention is to determine the optimum breeding pair from one or more stallions (males) and one or more mares (females) based upon a predetermined set of selection criteria. Such criteria might be size, color, dressage skills, rodeo skills, jumping height, ability as a draught horse, thoroughbred racing and other valuable or desired traits.

D. BRIEF DESCRIPTION OF THE SEVERAL VIEWS OF THE DRAWINGS

A better understanding of the present invention will be realized from the detailed description which follows, taken in conjunction with the accompanying drawings in which:

FIG. 1 is an example of a judge's score card from an equestrian event;

FIG. 2 is a sample of one page from one embodiment of a an owner's survey; and

FIG. 3 discloses depictions of a normal horse and two horses suffering from Lordosis.

E. DETAILED DESCRIPTION OF THE INVENTION

The present invention includes the following methods of generating information pertaining to various animals which can include show horses, quarter horses, and thoroughbreds. Though the following discussion is directed toward horses, the present invention can also be used with other valuable animals including but not limited to cattle (colloquially cows), sheep, dogs, camels, cats, pigs, and goats.

The methods enable the gathering of information which can be used in a) assessing the value/abilities of a horse that one anticipates purchasing—Performance Index, b) tracking the health status of a horse over time, and c) optimizing the breeding of a particular mare and stallion from a plurality of mares and stallions in order to maximum the probability of obtaining a foal having the desired characteristic(s).

E1. Categories

Each of these methods is based upon a compilation of one or more of the following five categories of scores which are obtained from 1) DNA/genetics analysis, 2) a compilation of show scores, 3) Conformation 4) Owner/trainer provided information about the horse and 5) Veterinary/clinical information about the horse. Each of these categories is discussed below.

1. DNA/Genetics

There are many well known genetics markers that can be measured to evaluate any number of physical traits and predisposition for physical skills, appearance and diseases. Genes that effect color and that can be tested for include but are not limited to:

| | | | | |
|---|---|---|---|---|
| Agouti | Black/Red | Brindle | Champagne | Cream |
| Dominant White | Frame Overo | Grey | Pearl | Sabino |
| Silver | Splashed White | Tobiano | White Spotting | |

In addition to genes for color, genes that indicate health and disease conditions or disease predispositions can include but are not limited to:

| Condition | Gene | Explanation |
|---|---|---|
| AIS | AR | Androgen sensitivity |
| Cereb. Abiotrophy | MUTHY | Cerebellar Abiotrophy |
| EAV Susceptibility | ECA11 | Equine Arteritis Viral susceptibility |
| FIS | SLC5A3 | Foal Immunodeficiency Syndrome |
| GBED | GBE1 | Glycogen Branching Enzyme Disorder |
| HERDA | PPIB | Hereditary Equine Regional DermalAsthenia |
| HYPP | SCN4A | Hyperkalemic Periodic Paralysis |
| IAR - Subfertility | FKBP6 | Subfertility allele |
| JEB1 | LAMC2 | Junctional Epidermolysa Bullosis |
| Lavender Foal Syndrome | MYO5A | Lavender Foal alleles |
| MH | RYR1 | Malignant Hyperthermia |
| Myotonia | CLCN4 | Myotonia alleles |
| PSSM | GYS1 | Polysaccharide Storage Myopathy |
| SCID | DNAPK | Severe Combined Immunodeficiency |
| West Nile | WNVR | West Nile Virus |
| Lordosis | ECA20 | Lordosis risk alleles |

In addition to health and disease, genes for performance and abilities include, but are not limited to:

| | | |
|---|---|---|
| Curiosity/Vigilance | DRD4 | Curiosity genes |
| Myostatin/speed | MSTN | Sprint ability |
| Gait | DMRT3 | Gaiting gene (loss of canter) |

Though there are known genetic markers that correlate with physical attributes new and additional markers can be identified be means the present invention which involves the correlation of various genetic data with behavioral data and show scores obtained from owners and judges of various events. By gathering and correlating both behavioral and genetic marker data, it is possible predict or anticipate the behavioral aspects of any animal based upon the genetic markers that can be measured.

Figure 1:
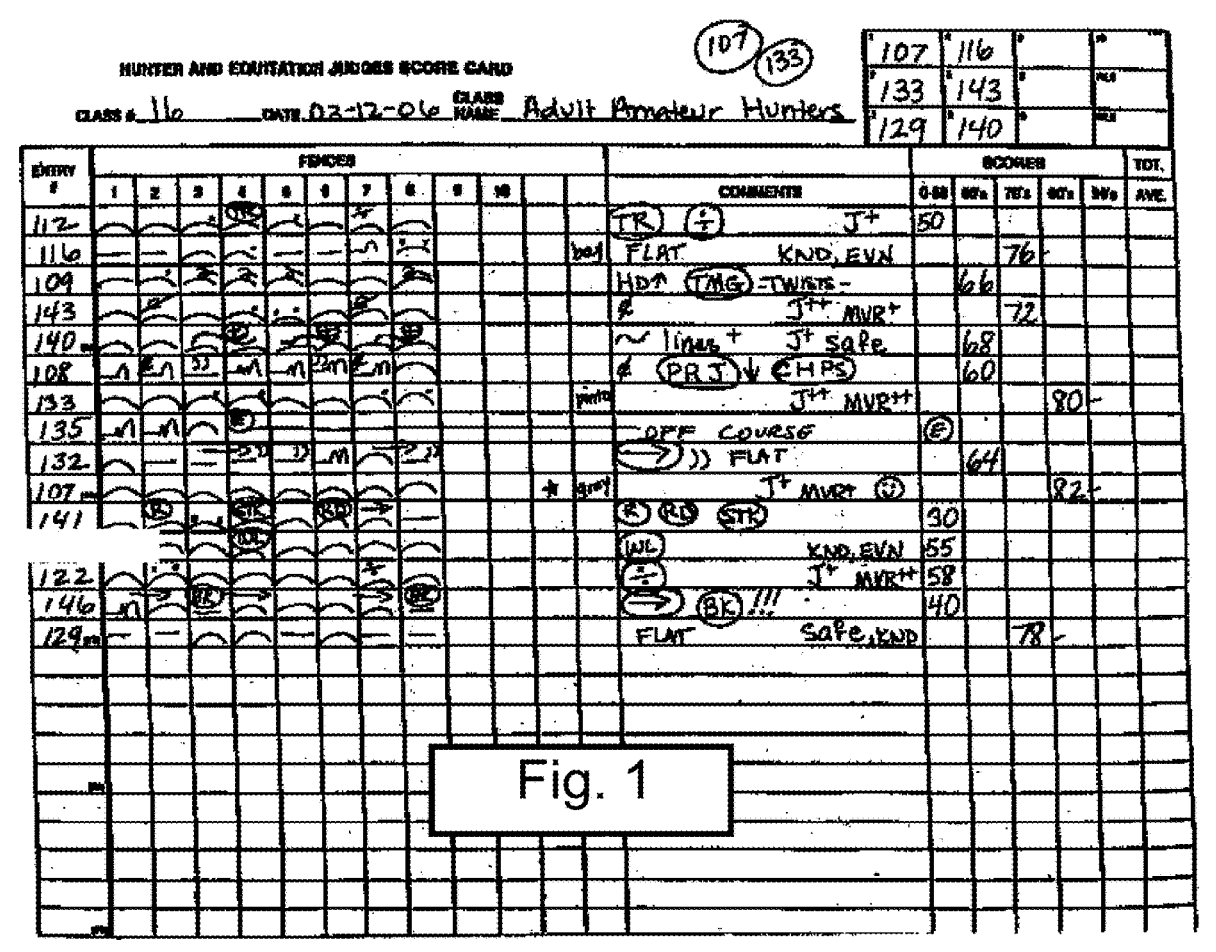

An example a judge's score card for horses (FIG. 1) and behavioral survey of an owners horse (FIG. 2) show the type of subjective and behavioral information that will be gathered and then correlated with the DNA data gathered as described below. As much behavioral information as possible is collected for each horse that will be tested. Typically 100-10,000 horses will be tested for each trait or condition of interest.

Next DNA samples will be collected and analyzed from the same horses from which behavioral data (show scores and owner/trainer feedback) has been gathered. The DNA samples can be collected from several types of tissues including, but not limited to hair, blood, saliva, buccal swabs, reproductive cells, skin samples and nail/hoof clippings. The samples will be extracted and tested for various genetic markers by various analytical techniques that are known to one skilled in the art.

Some behavioral traits have already been associated with certain genome sequences but those associations are not definitive. The analytical protocol of the present invention would include standard sequencing across the whole the length of one or more gene sequences or regions that are suspected or anticipated to be associated with a behavioral trait. In addition, the existence of single nucleotide polymorphisms, duplications, deletions and mutations in those sequences would be isolated and identified.

By correlating the behavioral data obtained from judges' score cards and owner surveys with the genetic marker and sequence data obtained by analysis of the tissue samples, the association of certain biochemical markers with the behavioral traits can be made.

Thus the collection and analysis of DNA from a particular animal can be used to identify the genetic markers present in that animal and thus allows for the evaluation of the predisposition of that animal to exhibit those behaviors and posses those capabilities associated with those genetic markers.

Such traits can include, but are not limited to high and low jumping skills, style, speed, endurance for short, medium or long distances, skill in multiple jumps, temperament, height at maturity, gait style, ability to perform in a given discipline, work ethics, neurosis, strengths, disease predisposition or resistance, and other traits.

This information will be very valuable in terms of horse value determination, assigning stud fees, discipline suitability, and selecting breeding pairs or cross-matches (in the event there are multiple stallions or mares to one horse as a potential match). In addition, by knowing the projected behavioral and skill set that a young horse possess, as determined by the genetic markers and diagnostic tests, the proper training regimen can be selected in order to maximize the horse's development while minimizing stress and illness.

2. Show Scores

Very often horses will be shown at various events and scored by judges on a vast array of characteristics. Judges will evaluate the horses based upon a standardized scoring and marking system used in official dressage, jumping events and other officially sanctioned events. The factors that are judged include but are not limited to the ability to jump, speed, quality of walk, trot and canter, and movement to music, temperament/submission, ability to cut cows, ability to display specialized gaits, ability to pull carts, racing (track and cross country), ability to change leads during canter or gallop, and the ability to maneuver around a course or objects. See FIG. 1 for an example of a scoring card.

3. Conformation

Conformation deals with the physical attributes of the horse and evaluates the horse's bone structure, musculature and body proportions in relation to each other and the intended use of the horse. A horse that is to be used a draught animal would need to have a different confirmation that one that will be used as a jumper or a cutting horse. Conformational traits may be measured in angles for shoulder, hip and neck set, as well as back length, leg length, pastern length and angle, height and weight, head and ear shape, musculature, hoof shape and hardness, shoulder versus hip height, and other characteristics.

4. Owner Feedback

Questionnaires have been generated which gather information from owners about specific behavior and skills for their horses. Questionnaires are directed to a number of traits which include, but are not limited to, spooking, jumping skill, speed, dressage, temperament and gaits or gait quality/ability.

In addition, questionnaires relating to the health of the horse are also gathered. Such questionnaires could include, but are not limited to information about the respiratory system, digestive system, lameness, and bacterial, fungal or viral susceptibility. See FIG. 2 for on page from an example of an owner's questionnaire.

5. Veterinary Diagnostics

This information is based upon a wide range of laboratory testing and various imaging techniques which could include, but not be limited to:

a. CBC—Complete Blood Count which includes white blood cell count, red blood cell count, hemoglobin level, hematocrit, platelet count and other blood cell morphology evaluations and measurements.

b. Various metabolic assays which could include but not be limited to blood sugar, protein, cholesterol, BUN, and IL6 (interleukin 6). These tests can provide an assessment of organ function (e.g., kidney, liver and muscle) and general body metabolism. IL-6 assays can identify chronic inflammatory conditions in older horses. Increased IL-6 values in humans correlate with greater/earlier mortality and cardiovascular complications.

c. DNA related tests such as the assay of telomere length provides additional insights into the present and future health of the animal which may include biological age, underlying health or disease, as well as prior health and possible lifespan.

d. Imaging techniques such as X-rays, computerized tomography (CT) scans and magnetic resonance imaging (MRI) can be used to gather sophisticated data about the condition and health of the horse.

e. Fibrinogen—This test is currently utilized in the detection of acute inflammation and may provide a measure of exercise status (too much, too little). Owners and trainers can then adjust the horses' exercise regimen specific to the animal tested.

f. Fecal Ulcer PCR—This test may provide a non-invasive, early diagnosis for ulcer onset and the results of which can provide the caregiver an appropriate solution, possibly preventing progression and unnecessary medication.

g. Transthyretin (TTR)—An assay that provides short-term nutritional status by measuring the concentration of transthyretin in the blood. Transthyretin's concentration more closely reflects recent dietary intake rather than overall nutritional status providing a glimpse into the proper feeding regimen for the animal athlete being monitored.

Each of the criteria is given a weighted value in terms of calculating the overall Performance Index. The value assigned to each of these five categories is based upon the intended use of the animal which dictates the type of Performance Index that will be generated. Furthermore the value assigned is a subjective measurement assigned by the experienced technician and based upon that technician's knowledge, the database information collected on that animal, its current experience, performance, and the type of Performance Index being generated.

Below is a sample Performance Index Report for a jumping horse. The Performance Index is based upon gathering the information needed to evaluate a jumping horse. This would include specific gene assays, lab tests and owner survey questionnaires directed to the traits needed for a good jumping horse.

| Category | Percent of Total Index | Score for each Category |
| --- | --- | --- |
| 1. DNA | 45% | 60/100 |
| 2. Show Scores | 25% | 80/100 |
| 3. Conformation | 10% | 100/100 |
| 4. Owner Feedback | 5% | 100/100 |
| 5. Veterinary Diagnostics | 15% | 70/100 |

The overall Performance Index for this example would be 82/100 which is the arithmetic average of all of the values in the third column.

Each Performance Index is designed to assess certain and specific traits. In order to achieve that, specific factors in each of the five categories are used. For example, Conformation would be judged differently for horse that would have different uses. The Owner Feedback Questionnaires would ask different questions if the horse were to be a dressage horse as opposed to a reining, cutting, racing, or a jumping horse.

A Performance Index can be repeated at desired intervals in order to measure the health, aging and training effectiveness of an animal.

E2. Breeding Cross-Match Evaluations

The information obtained from the five categories discussed about can be used for other purposes such as Breeding Cross-Match Evaluations. Many times a horse owner is looking to obtain a horse with certain characteristics. It is possible to evaluate a specific mare and stallion to determine what the likelihood of the offspring of that breeding or cross would yield a horse having the specific characteristic that the owner is looking for. It may be color, temperament, size, conformation, speed, height, disease avoidance or soundness as well as any other characteristic that can be measured as described in the five categories given above. It may also be a situation in which the owner already owns a horse and wants to identify a breeding animal that would provide the best chance of the desired offspring.

For example: If someone would desire a Palomino reining horse, they would require that the stallion and the mare would be able to contribute to the offspring the genes for Sprinting speed (found in the myostatin gene) as well as the combination of a Red based coat with one Cream gene to dilute it to Palomino (a golden yellow color). The breed matching database would then be searched for horses with those qualifications as potential matches to the planned breeding: A mare with Red coat (genetically denoted as "e/e") and Sprint Type myostatin genes (genetically denoted as "C/C") could be matched with a stallion whose genetic Sprint type was also "C/C", his base coat color as "e/e" however, he would ALSO need to have the Cream modifier (denoted as "Cr") in order to produce the Palomino color in the foal:

Scenario #1
   Mare: Coat Color e/e (Red) and Sprint Speed (C/C) X
   Stallion A: Coat Color e/e, Cr/Cr and Sprint Speed (C/C)=Foal with e/e, Cr/n, C/C (a Sprint type speed with Palomino color) 100% of the time Scenario #2
   Mare: Coat Color e/e (Red) and Sprint Speed (C/C) X
   Stallion B: Coat Color E/e (Black "E" and Red "e") Cr/Cr and Sprint Speed (C/C)=Foal with e/e, Cr/n, C/C (a Sprint type speed with Palomino color) 50% of the time Foal with E/e, Cr/n, C/C (Sprint type speed with Smokey Black color) 50% of the time Scenario #3
   Mare: Coat Color e/e (Red) and Sprint Speed (C/C) X
   Stallion C: Coat Color e/e, Cr/Cr and Mid-distance Speed (C/T)=Foal with e/e, Cr/n, C/C (a Sprint type speed with Palomino color) 50% of the time Foal with e/e, Cr/n, C/T (a Mid-distance type speed with Palomino color) 50% of the time Therefore, the function of the Breed Match is to utilize the genetic analysis, performance information, math and science to increase probabilities of the desired offspring while reducing the probabilities of inducing disease and unwanted animals.

E2.1. Example of Breed Cross-Match Service for Purposes of Performance Enhancement and Disease Prevention
Condition of interest: Lordosis (Swayback)
Definition: Lordosis is a curvature or dip in the spine that is often seen in older horses.
However, in the American Saddlebred, this condition also affects younger horses. These animals do not appear to experience pain from their condition and are still able to be used under saddle.
However, certain animals can have an extreme form of swayback making saddle fitting and pregnancy (carrying a foal) difficult and often not possible. See FIG. 3.

The Lordosis genotype of the following allele calls in the four known regions L1 (BIEC2-53523), L2 (BIEC2-532534), L3 (BIEC2-532578) and L4 (BIEC-532658) detected as L1: TT, L2: GG, L3: TT, L4: GG show high correlation and indication of the homozygous recessive condition illustrated in Example Horses 2 and 3 in FIG. 3.

According to the literature and research, 80% of horses with this genotype will exhibit the phenotype (physical condition) and all will pass it on to offspring 100% of the time. However, if properly matched with a genetically known mate, one with as little as ONE variation in ONE of the four alleles, the breeding of that particular combination will not allow the condition to exist in the offspring.

Example 1

Male affected genotype: $TT/GG/TT/GG \times$ Female affected genotype

: $TT/GG/TT/GG$ =100% offspring with Lordosis, or $TT/GG/TT/GG$ genotype and,

80% with the physical affliction (phenotype)

Example 2

However, if the same affected male is bred with a known female with one difference in the alleles:

Male affected genotype:

$TT/GG/TT/GG \times$ Female non-affected genotype:

$TT/GG/TT/GA$ = 50% offspring with Lordosis genotype and high likelihood of phenotype Furthermore, if the same affected male is bred with a known female non-affected (completely non-lordosis type, even in only ONE allele set), then the foal will NOT be a carrier or affected. The disease/condition is eliminated from the offspring and eventually the bloodline.

Example 3

Male affected genotype: $TT/GG/TT/GG \times$ Female non-affected genotype $TT/GG/TT/AA$ = Offpsring, missing the possibility of "GG" allele match in L4 region and so, none affected. However the offspring remains as "carrier" and can still pass the Lordosis trait without proper genetic breed matching until one entire allele region is altered: $TT/GG/TT/GA$ Therefore, when breeding horses with afflictions, colors or abilities (i.e., speed or jumping) and a known allele set can be revealed, a breed match service will reveal the alleles/sets or alleles in any given region(s) having to do with the desired/undesired trait and provide the safest/best breeding options for any given animal in a simple cross-match chart. For example:

| MARE'S NAME: Marquese IV | | | | | | | |
|---|---|---|---|---|---|---|---|
| | TRAIT | | | | | | |
| | LWO | SCID | SWAY-BACK | LFS | GAIT | SPEED | COLOR |
| Stallion 1 | ✓ | ✓ | ✓ | ✓ | ✓ | ✓ | ✓ |
| Stallion 2 | ✓ | ✗ | ✓ | ✓ | ✓ | ✓ | ✓ |
| Stallion 3 | ✗ | ✓ | ✓ | ✓ | ✓ | ✓ | ✓ |
| Stallion 4 | ✓ | ✓ | ✓ | ✓ | ✓ | ★ | ★ |
| Stallion 5 | ✓ | ✓ | ✗ | ✗ | ✓ | ✓ | ✓ |
| Stallion 6 | ✓ | ✓ | ✓ | ✓ | ✓ | ✓ | ★ |

✓ = No complications
✗ = Bad—serious disease, physical condition or death
★ = Very good combination, desired result/trait Based on this sample cross-breeding, a general ranking of the stallions is shown in the table below. However, in cases where specific traits are highly desirable, the ranking order could be different.

| | ★ | ✓ | ✗ |
|---|---|---|---|
| Stallion 4 | 2 | 5 | 0 |
| Stallion 6 | 1 | 6 | 0 |
| Stallion 1 | 0 | 7 | 0 |
| Stallion 2 | 6 | 0 | 1 |
| Stallion 3 | 6 | 0 | 1 |
| Stallion 5 | 5 | 0 | 2 |

F: EXAMPLE OF THE REPORT FORMAT FROM ONE PANEL OF THE PRESENT INVENTION

HORSE INFORMATION

| | |
|---|---|
| Horse ID | DOB |
| Horse Name | Age |
| Breed Name | Sex |
| Color | Height |
| Discipline | Prior Test |

REGISTRY INFORMATION

Registry
Registry Number
Known Issues
Sire
Sire Registry Number
DAM
DAM Registry Number
Contact OK?
Owner
Contact Person
Phone #
Email
Address Test Info (YourHorse is a fictitious name used to protect the confidentiality of the owner and horse as given in the actual report provided below.)

YourHorse is a black or dark bay horse with the capability of passing on the colors Black (E), Red (e), and white markings (DW20—the coat pattern allele that may add white markings to her coat and appear similar to "Splashed White") to offspring. While many forms of white can be lethal to foals when inherited from both parents, the DW20 variety is known not to be lethal as either homozygous (two copies of the same gene) or heterozygous (one copy from one parent and none from the other).

- As YourHorse has a single copy of the DW20 gene for white markings, she can pass this on to 50% of all offspring.
- 50% of her foals can inherit Red (e) or "Chestnut".
- 50% of her foals can inherit Black (E).
- 100% of her foals can inherit Agouti (Bay), only visible on a Black base coat.
- She is also homozygous for the GAITED or "Loss of Canter" gene and will pass the Gaited gene on to 100% of all offspring.

Results

| Traits | Pos/Neg | Phenotype or Description |
|---|---|---|
| Agouti | +/+ A/A | Agouti Detected (Homozygous) appears Brown or Bay |
| Black/Red | +/− Ee | Black Factor detected: Red Factor detected Horse appears black or dark brown in absence of modifiers |
| Brindle | −/− | No Brindle Detected |
| Dominant White | −/+ DW20 | White detected. May have white markings; non-lethal form of dominant white when passed to offspring |
| Splashed White Sabino 1 | −/ | No Splashed White detected Inconclusive |
| Macchiato | −/− | No Macchiato detected |
| White Spotting | −/− | No White Spotting detected |
| Champagne | −/− | No Champagne detected |
| Cream Dilution | −/− | No Creme detected |
| Silver (Ocular Defect) | −/− | No Silver detected |
| Overo (Lethal White) | −/− | No Lethal White Overo detected |
| Lavendar Foal | −/− | No Lavendar Foal detected |
| S.C.I.D. | −/− | No Severe Combined Immunodeficiency detected |
| Equine Viral Arteritis | Resistant | A/A/G/G/A/G/CT |
| Myotonia | −/− | No Myotonia detected |
| Subfertility | −/− | Normal, non-reduced |
| Androgen Insensitivity | −/− | No Androgen Insensitivity detected |
| PSSM | −/− | No Polysaccharide Storage Myopathy detected |
| Epidermolysis Bullosa | −/− | No Epidermolysis Bullosa detected |
| Cerebellar Abiotrophy | −/− | No Cerebellar Abiotrophy detected |
| F.I.S. | −/− | No Foal Immunodeficiency Syndrome detected |
| H.E.R.D.A. | −/− | No Hereditary Equine Regional Dermal Asthenia detected |
| Malignant Hyperthermia | −/− | No Malignant Hyperthermia detected |
| H.Y.P.P. | −/− | No Hyperkalemic Periodic Paralysis detected |
| West Nile Virus (normal v. high risk) | | "Normal" risk haplotype detected |
| Lordosis | CC/AA/ TC/GT | No Lordosis detected |
| Curiosity/ Vigilance | | Inconclusive |
| Myostatin/Speed | T/T | Horse displays endurance/distance haplotype |

G. SINGLE SOURCE FOR MULTI-FACTOR ASSESSMENT

A critical element of the present invention involves the combination of many various clinical tests in a single panel that can be ordered and paid for from a single vendor. Previously, an owner would need to arrange for tests with a wide range of vendors in order to achieve the comprehensive set of data that the panel of the present invention provides by itself and many of the tests are simply not available on the market today. In addition, questions and follow-up can be conducted with the single vendor. This facilitates comprehensive discussion and communication with the owner of the animal which results in a more meaningful and coordinated discussion of the results of the panel.

Though discussed above primarily in reference to the testing of horses, the methods of the described invention can be applied to a wide range of other animals including but not limited to cattle, sheep, goats, dogs, camels, cats, pigs, goats as well companion, laboratory and service animals.

The various behavioral traits that are evaluated, as well as the genetic markers to be searched for, identified and correlated, will be selected to be appropriate for the particular animal and the animal's intended use.

What is claimed is:

1. A method for producing a non-human offspring animal with a plurality of predetermined traits comprising the steps of:
   (A) generating data about a first non-human animal prepared by:
      (i) performing genetic tests to determine the genotype of the first animal for each of the following genetic markers:
         (a) a coat color gene selected from the group consisting of agouti, black/red, brindle, champagne, cream, dominant white, frame overo, grey, pearl, sabino, silver, splashed white, tobiano, and white spotting,
         (b) a curiosity gene that is a dopamine D4 receptor (DRD4) gene,
         (c) a speed gene that is myostatin (MSTN) gene, and
         (d) a gait gene that is a doublesex and mab-3 related transcription factor 3 (DMRT3) gene; and
      (ii) gathering information about the predetermined traits of the first animal by:
         (a) obtaining information from someone knowledgeable about the first animal pertaining to the plurality of predetermined traits,
         (b) performing one or more clinical assays of biological tissue obtained from the first animal pertaining to the plurality of predetermined traits, and
         (c) performing one or more diagnostic tests on the first animal pertaining to the plurality of predetermined traits, and, optionally,
         (d) obtaining scores assigned to the first animal during a competition pertaining to the plurality of predetermined traits;
   (B) using the data and information of steps (A)(i) and (A)(ii) to establish an overall assessment of the first animal;
   (C) analyzing a breed matching database to identify a second non-human animal of the opposite sex from the first animal having an overall assessment produced using the same data and information as was determined for the first animal, whereby a comparison of the overall assessment of the first animal with the overall assessment of the second animal indicates that breeding the second animal with the first animal would produce the non-human offspring animal with the predetermined traits; and
   (D) breeding the first animal with the second animal to produce the non-human offspring animal having the plurality of predetermined traits.

2. The method of claim 1, wherein the overall assessment of the first or second animal relates to an intended use of the offspring animal.

3. The method of claim 1, wherein the offspring animal, the first animal, and the second animal are selected from the group consisting of horses, cattle, sheep, dogs, camels, cats, pigs, goats, companion animals, service animals and laboratory animals.

4. The method of claim 1, wherein said method further comprises performing genetic tests to determine the genotype of the first animal and/or the second animal for each of the following genetic markers: ECA11, SLC5A3, GBEI, PPIB, SCN4A, FKBP6, LAMC2, MYO5A, RYR1, CLCN4, GYS1, DNAPK, WNVR, and ECA20.

5. The method of claim 1, wherein the method further comprises determining a purchase or sales price for the first animal, the second animal, and/or the offspring animal.

6. A method of producing an offspring non-human animal having a plurality of predetermined traits comprising breeding a first animal having the plurality of predetermined traits with a second animal of the opposite sex having the plurality of predetermined traits, wherein the first animal and the second animal have been determined to have the plurality of predetermined traits according to steps A-C of the method of claim 1.

7. A method for breeding a first non-human animal and a second non-human animal of the opposite sex of a predetermined species to produce a non-human offspring animal comprising the steps of:
   (A) searching a breed matching database to identify the first animal of said species having a plurality of predetermined traits, wherein the plurality of predetermined traits are determined by:
      (i) performing genetic testing to determine the genotype of the first animal for each of the following genetic markers:
         (a) a coat color gene selected from the group consisting of agouti, black/red, brindle, champagne, cream, dominant white, frame overo, grey, pearl, sabino, silver, splashed white, tobiano, and white spotting,
         (b) a curiosity gene that is a dopamine D4 receptor (DRD4) gene,
         (c) a speed gene that is myostatin (MSTN) gene, and
         (d) a gait gene that is a doublesex and mab-3 related transcription factor 3 (DMRT3) gene; and
      (ii) gathering information about the plurality of predetermined traits of the first animal by:
         (a) obtaining information from someone knowledgeable about the first animal pertaining to the plurality of predetermined traits,
         (b) performing one or more clinical assays of biological tissue obtained from the first animal pertaining to the plurality of predetermined traits, and
         (c) performing one or more diagnostic tests on the first animal pertaining to the plurality of predetermined traits, and, optionally,
         (d) obtaining scores assigned to the first animal during a competition pertaining to the plurality of predetermined traits;
   (B) searching the breed matching database to identify the second animal of said species having the plurality of predetermined traits, wherein the plurality of predetermined traits are determined according to the method of steps (A)(i) and (A)(ii);
   (C) based upon the searching of steps (A) and (B), using the breed matching database to perform an analysis of potential offspring resulting from the breeding of the first animal with the second animal;
   (D) based upon the searches of steps (A) and (B) and the analysis of step (C), selecting the first animal that could potentially produce an offspring animal having the plurality of predetermined traits;
   (E) based upon the searches of steps (A) and (B) and the analysis of step (C), selecting the second animal that could potentially produce an offspring animal having the plurality of predetermined traits; and
   (F) breeding the first animal with the second animal.

8. The method of claim 7, wherein only the first animal is assessed.

9. The method of claim 7, wherein only the second animal is assessed.

* * * * *